(12) United States Patent
Bierhoff

(10) Patent No.: US 8,702,743 B2
(45) Date of Patent: Apr. 22, 2014

(54) INSTRUMENT WITH AN INFLATABLE BALLOON

(75) Inventor: Waltherus Cornelis Jozef Bierhoff, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 711 days.

(21) Appl. No.: 12/446,251

(22) PCT Filed: Oct. 18, 2007

(86) PCT No.: PCT/IB2007/054234
§ 371 (c)(1),
(2), (4) Date: Apr. 20, 2009

(87) PCT Pub. No.: WO2008/050263
PCT Pub. Date: May 2, 2008

(65) Prior Publication Data
US 2010/0318027 A1    Dec. 16, 2010

(30) Foreign Application Priority Data
Oct. 25, 2006  (EP) ..................................... 06122935

(51) Int. Cl.
*A61M 29/00* (2006.01)
(52) U.S. Cl.
USPC ...... 606/191; 606/192; 604/96.01; 604/97.01
(58) Field of Classification Search
USPC ..................... 606/45–52, 191–198, 205–210; 604/96.01, 97.01; 607/101, 102, 116, 607/133
See application file for complete search history.

(56) References Cited

U.S. PATENT DOCUMENTS

| | | | |
|---|---|---|---|
| 4,790,310 A | 12/1988 | Ginsburg et al. | |
| 4,913,142 A | 4/1990 | Kittrell et al. | |
| 5,066,292 A | 11/1991 | Muller et al. | |
| 5,112,347 A * | 5/1992 | Taheri | 606/200 |
| 5,176,693 A | 1/1993 | Pannek | |
| 5,195,507 A * | 3/1993 | Bilweis | 600/204 |
| 5,395,361 A | 3/1995 | Fox et al. | |
| 5,451,221 A | 9/1995 | Cho et al. | |
| 5,746,738 A | 5/1998 | Cleary et al. | |
| 5,814,016 A * | 9/1998 | Valley et al. | 604/96.01 |
| 5,865,802 A * | 2/1999 | Yoon et al. | 604/104 |
| 6,106,515 A | 8/2000 | Winston et al. | |
| 6,106,550 A | 8/2000 | Magovern et al. | |
| 6,156,029 A | 12/2000 | Mueller | |
| 6,409,723 B1 * | 6/2002 | Edwards | 606/41 |
| 6,409,732 B1 * | 6/2002 | Salyer | 606/91 |
| 6,516,216 B1 | 2/2003 | Fontenot et al. | |
| 6,620,181 B1 * | 9/2003 | Bonutti | 606/190 |
| 6,746,463 B1 | 6/2004 | Schwartz | |
| 6,964,661 B2 * | 11/2005 | Rioux et al. | 606/41 |

(Continued)

FOREIGN PATENT DOCUMENTS

| WO | 8907423 A1 | 8/1989 |
|---|---|---|
| WO | 2006038247 A1 | 4/2006 |

*Primary Examiner* — Katherine Dowe
*Assistant Examiner* — Sidharth Kapoor

(57) ABSTRACT

A medical instrument including an inflatable balloon and a plurality of filamentary tool elements with a proximal movable section that is attached to a wall of the balloon and with a distal end projecting freely from the balloon, wherein the proximal end forms a substantially cylindrical shape when the inflatable balloon is inflated and deflated and the distal end bends inwards from the substantially cylindrical shape when the balloon is deflated.

12 Claims, 6 Drawing Sheets

(56) References Cited

U.S. PATENT DOCUMENTS

| | | |
|---|---|---|
| 7,125,407 B2 * | 10/2006 | Edwards et al. .............. 607/133 |
| 7,396,329 B2 * | 7/2008 | Nakao ........................... 606/192 |
| 2001/0025175 A1 | 9/2001 | Panescu et al. |
| 2003/0055400 A1 | 3/2003 | Seward et al. |
| 2003/0158563 A1 | 8/2003 | McClellan et al. |
| 2003/0225433 A1 * | 12/2003 | Nakao ........................... 606/191 |

* cited by examiner

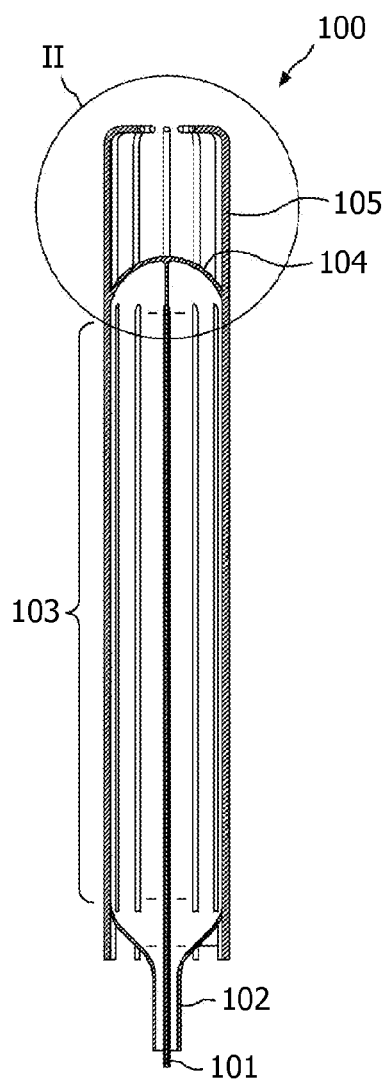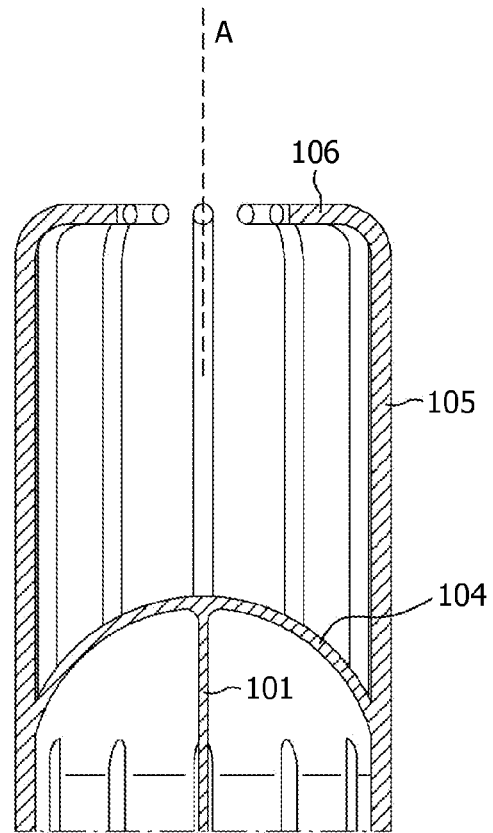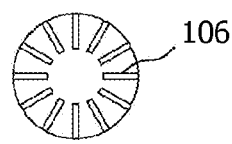
FIG. 1A
FIG. 2
FIG. 1B

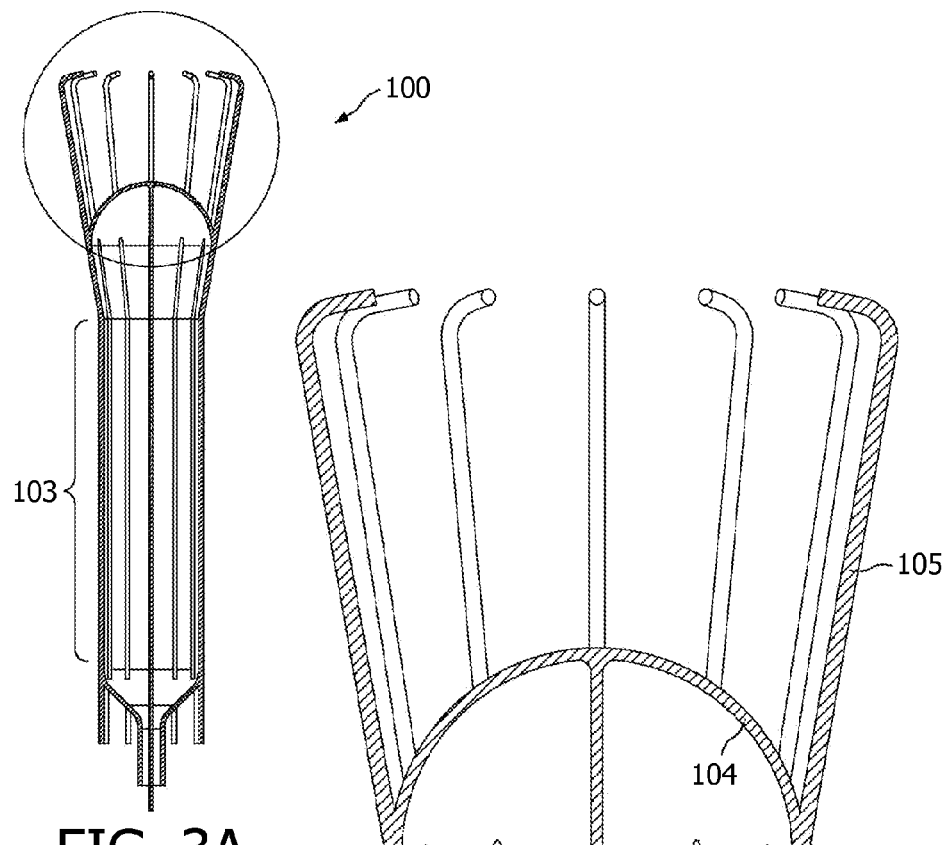
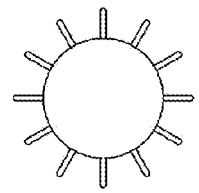
FIG. 3A
FIG. 3B
FIG. 3C

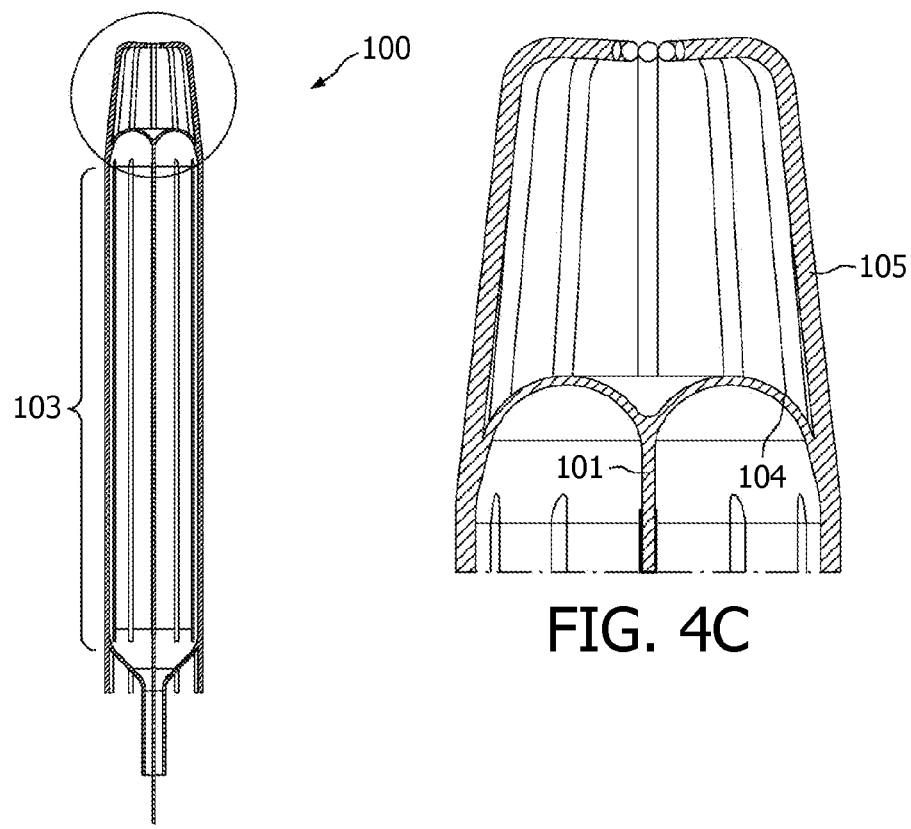
FIG. 4C
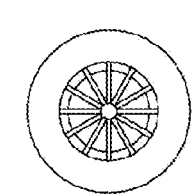
FIG. 4A
FIG. 4B

INSTRUMENT WITH AN INFLATABLE BALLOON

This application is a National Stage of International Application No. PCT/IB2007/054234, filed Oct. 18, 2007, which claims the benefit of European Patent Application (EPO) No. 06122935.7, filed Oct. 25, 2006.

FIELD OF THE INVENTION

The invention relates to an instrument with an inflatable balloon that is particularly suited for medical procedures like minimal invasive surgery, and to a system comprising such an instrument. Moreover, it relates to a method for moving a tool element in e.g. minimal invasive surgery.

BACKGROUND OF THE INVENTION

From the U.S. Pat. No. 6,106,550 a catheter is known that comprises a radially folded tip and a plurality of axially extending optical fibers which are attached to the walls of the catheter. An annular balloon at the tip of the catheter can be inflated to unfold and extend the catheter tip in order to adapt it to the size of a blood vessel to be treated.

SUMMARY OF THE INVENTION

Based on this background, it was an object of the present invention to provide alternative means for the manipulation of objects in for example minimal invasive surgery, wherein it is desirable that tool elements can be moved over a significant range with comparatively simple means.

This object is achieved by an instrument according to claim 1, a system for minimal invasive surgery according to claim 11, and a method according to claim 12. Preferred embodiments are disclosed in the dependent claims.

The instrument according to the present invention may serve for any purpose in e.g. science, industrial production, robotics etc. It is particularly suited for medical procedures like minimal invasive surgery. The instrument comprises the following components:

a) An inflatable balloon as it is known for example from the field of medical catheters, where such balloons are used to dilate vessels or to place and extend stents. In principle, the inflatable balloon may have any topology, though simple spheroidal or toroidal topologies are preferred. Typical materials for the inflatable balloon are physiologically acceptable and may e.g. comprise a latex rubber.

b) At least one tool element with a movable section that is solely attached to the wall of the balloon. While said section is typically attached to the outer side of the balloon, there may also be applications in which it is attached to the inner side of the balloon.

The described instrument has the advantage that its tool element can be moved over a large range because it is with at least one section solely attached to the wall of the balloon such that this section can in principle completely follow the movement of said wall. When the balloon is inflated or deflated, the tool element will therefore shift and typically also change its orientation accordingly. In contrast to this, tool elements like the optical fibers described in U.S. Pat. No. 6,106,550 are more or less firmly embedded in some carrier structure that severely restricts their movement and largely decouples it from the associated balloon.

While in general there are no restrictions as to the size and function of the tool element, said tool element will have in many applications a substantially filamentary and flexible configuration. Such a tool element can have a performance like a finger that can be bent or stretched if the associated balloon is deflated or inflated.

In a particular embodiment of the invention, the (filamentary, flexible) tool element comprises a wire. Said wire may preferably have a free end portion that projects from the balloon and that can be used to manipulate objects.

According to a further development of the aforementioned embodiment, the wire has an end portion with a barb, a bending or the like, wherein said end portion preferably projects freely from the balloon. Designing the end portion in such a way optimizes the tool element for certain functions. If for example a bent tool element cooperates with at least one counterpart (e.g. a further similar tool element), it can be used like a pince gripper for grabbing an object.

In another embodiment of the invention, the (filamentary) tool element comprises an optical fiber. Light can then be conducted through the fiber and emitted from its end into the surroundings for purposes of e.g. illumination or for cutting tissue with a laser beam. By inflating or deflating the balloon, the emission of the optical fiber can selectively be focused within a large range.

Of course the described embodiments of the invention with wires and optical fibers as tool elements can be combined. Thus a balloon may for example carry an alternating sequence of optical fibers and wires on its outer wall, wherein the fibers can illuminate the operating field of the wires.

While the invention was up to now described including the case of an instrument with just one tool element, preferred embodiments of the invention comprise a circumferential arrangement of a plurality of (similar or differently designed) tool elements around the balloon. Thus a radial symmetry of the arrangement around the axis of the balloon can be achieved. If wires are used as tool elements, at cage-like grabber can be realized. If optical fibers are used as tool elements, their outlets can be positioned on a circle of variable radius, and their emissions can be adjusted continuously between a convergent and a divergent direction.

In another embodiment of the invention, the instrument comprises a rigid body to which a further section of the tool element is attached. In an optional modification of this design, the balloon is at least partially connected to said rigid body. If the tool element is attached both to the rigid body and the flexible balloon, a flexion of the tool element can be realized. The rigid body can serve in this case as a stationary base to which for example the body of a wire or of an optical fiber is attached, while the tip of this tool element moves according to the filling state of the balloon.

In a further development of the invention, the instrument comprises a manipulating element that is fixed with one end to the wall of the balloon for selectively exerting forces onto said wall. The manipulating element may particularly be located within the balloon and be fixed to the inner wall of the balloon, and it may optionally be realized as a cord or a rod. Pulling on such a cord or pulling or pushing on such a rod can then selectively change the shape of the balloon without changing its state of inflation. Thus a further degree of freedom is achieved for the manipulation of the tool element attached to the balloon, which increases the functionality of the instrument.

The instrument may optionally further comprise a tubular element in which the balloon is disposed. The tubular element provides a shelter and a kind of skeleton for the balloon. The balloon is preferably not fixed to the tubular element but axially movable with respect to it.

The invention further relates to a system for minimal invasive surgery, said system comprising an endoscope or a catheter and a medical instrument of the kind described above (i.e. an instrument with an inflatable balloon and at least one tool element with a movable section that is solely attached to the wall of the balloon).

Moreover, the invention relates to a method for moving a tool element of an instrument for minimal invasive surgery, wherein a movable section of the tool element is attached to a balloon and wherein said balloon is inflated or deflated to produce a corresponding movement of the tool element.

The system and the method for minimal invasive surgery comprise the essential features of an instrument of the kind described above. Therefore, reference is made to the preceding description for more information on the details, advantages and improvements of that system and method.

BRIEF DESCRIPTION OF THE DRAWINGS

These and other aspects of the invention will be apparent from and elucidated with reference to the embodiment(s) described hereinafter. These embodiments will be described by way of example with the help of the accompanying drawings in which:

FIG. 1A shows schematically an axial section through of an instrument with a cage-like grab formed from wires;

FIG. 1B shows schematically a top view of an instrument with a cage-like grab formed from wires;

FIG. 2 shows an enlarged view of the tip area of the instrument that is encircled in FIG. 1, wherein the grab is in its neutral configuration with the wires extending axially;

FIG. 3A shows an axial section of the instrument of FIG. 1 in a state in which the balloon is inflated and the grab is opened;

FIG. 3B shows a top view of the instrument of FIG. 1 in a state in which the balloon is inflated and the grab is opened;

FIG. 3C shows an enlarged view of the tip of the instrument of FIG. 1 in a state in which the balloon is inflated and the grab is opened;

FIG. 4A an axial section of the instrument when the balloon is deflated and the grab is closed;

FIG. 4B shows a top view of the instrument when the balloon is deflated and the grab is closed;

FIG. 4C shows an enlarged view of the tip of the instrument when the balloon is deflated and the grab is closed;

Like reference numbers or numbers differing by integer multiples of 100 refer in the Figures to identical or similar components.

DETAILED DESCRIPTION OF EMBODIMENTS

In the following, the invention will be explained with respect to an application at catheters. The invention can however also be used in other medical applications (e.g. in endoscopes and the working area of endoscopes) as well as in a non-medical applications.

A catheter is an important tool for modern minimal invasive interventions. It is essentially a tube that can be inserted into a body cavity or blood vessel, thereby allowing easy access to critical positions of the body. Catheters are being used for diagnostics and therapy of predominantly cardiovascular diseases, e.g. placing stents in blood vessels, but also for urinary and neurovascular applications.

When a loose object has to be removed in a minimal invasive intervention, it has to be grasped. If this object is very fragile, soft, very hard, slippery, slimy or small, it is often hard to grab it with a pliers without pressing it into pieces.

In other applications of catheters, light coming from optical fibers is used to coagulate tissue for example in the cardiac area. Aiming the light onto a location and spreading the light over a variable surface poses a non-trivial problem in this case.

FIGS. 1A, 1B, 1C, 2, 3A, 3B 3C, 4A, 4B and 4C illustrate a first embodiment of an instrument 100 that addresses the above mentioned issues.

Figure 1C:
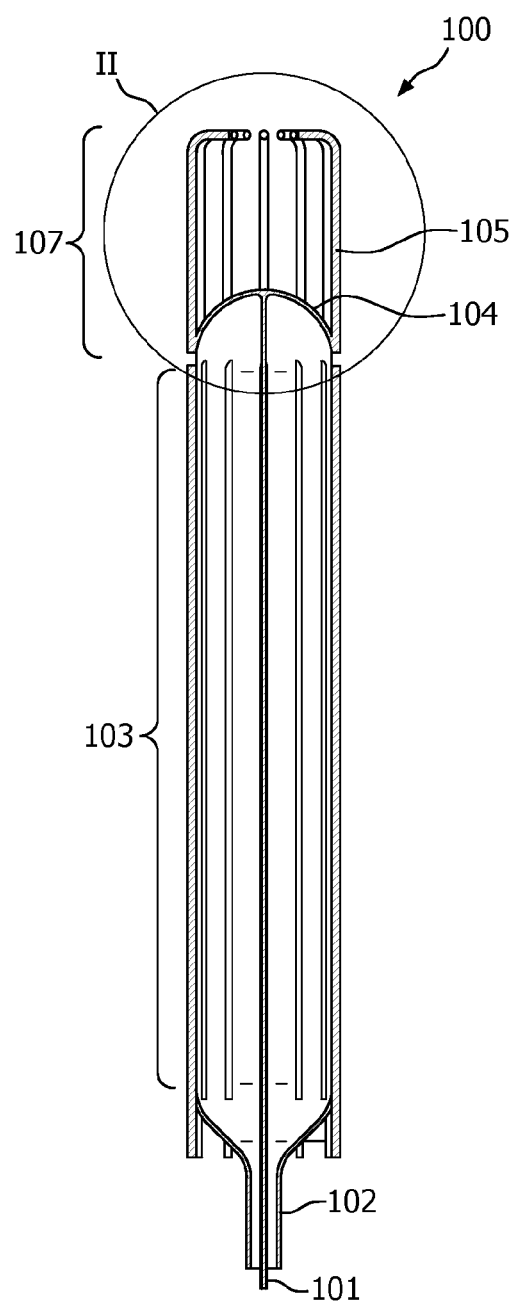
FIG. 1C shows schematically an axial section through of an instrument with a cage-like grab with a movable section that is solely attached to a wall of a balloon.

Specifically, FIG. 1A shows schematically an axial section through of an instrument with a cage-like grab formed from wires. FIG. 1B shows schematically a top view of an instrument with a cage-like grab formed from wires. FIG. 1C shows schematically an axial section through of an instrument with a cage-like grab with a movable section that is solely attached to a wall of a balloon. FIG. 2 shows an enlarged view of the tip area of the instrument that is encircled in FIG. 1, wherein the grab is in its neutral configuration with the wires extending axially. FIG. 3A shows an axial section of the instrument of FIG. 1 in a state in which the balloon is inflated and the grab is opened. FIG. 3B shows a top view of the instrument of FIG. 1 in a state in which the balloon is inflated and the grab is opened. FIG. 3C shows an enlarged view of the tip of the instrument of FIG. 1 in a state in which the balloon is inflated and the grab is opened. FIG. 4A an axial section of the instrument when the balloon is deflated and the grab is closed. FIG. 4B shows a top view of the instrument when the balloon is deflated and the grab is closed. FIG. 4C shows an enlarged view of the tip of the instrument when the balloon is deflated and the grab is closed.

Said instrument 100 comprises the following components:

An inflatable balloon 104 that is shown in FIGS. 1A, 1B, 1C and 2 in its "neutral" or resting state in which it has substantially a cylindrical shape and in which its distal tip has the same diameter as its body. At its proximal end, the balloon 104 comprises an inlet 102 that it is continued by a channel leading to some controllable supply (not shown) of gas or liquid, e.g. a physiological solution, by which the balloon can be inflated or the deflated. Balloons of the shown type are principally known from for example percutaneous angioplasty.

A plurality of linearly extending wires 105, wherein a subsection 107 of these wires 105 forms a movable section that is attached to the balloon 104. The wires are further equally distributed over the circumference of the balloon 104 and for instance provided with tips 106 that are radially bent inwards to the axis A of the balloon. In general, the ends 106 can have a variety of shapes. Depending on the application, they can for example be smooth (as shown) or have a barb.

A rigid body 103, which is substantially cylindrical in the depicted case, wherein a large part of the wall of the balloon 104 is attached to this rigid body. When the balloon is inflated for deflated, the rigid body 103 will keep its shape (cf. FIGS. 3A, 3B, 3C and 4A, 4B, 4C).

A pulling cord 101 that runs within the balloon 104 along the axis A and that is fixed to the tip of the balloon.

The wires 105 of the described instrument 100 realize a cage-like grab that can be manipulated by inflating or deflating the balloon and additionally by pulling the cord 101. FIGS. 1A, 1B, 1C and 2 show in this respect the neutral state of the grab with the wires extending linearly.

FIG. 1C shows the instrument 100 with at least one tool element (e.g., wires 105) with the movable section 107 that is solely attached to a wall of a balloon 104. While said section is typically attached to the outer side of the balloon, there may also be applications in which it is attached to the inner side of the balloon. The described instrument has the advantage that its tool element can be moved over a large range because it is with at least one section solely attached to the wall of the balloon such that this section can in principle completely follow the movement of said wall. When the balloon is inflated or deflated, the tool element will therefore shift and typically also change its orientation accordingly. While in general there are no restrictions as to the size and function of the tool element, said tool element will have in many applications a substantially filamentary and flexible configuration. Such a tool element can have a performance like a finger that can be bent or stretched if the associated balloon is deflated or inflated.

FIGS. 3A, 3B, 3C show the state of the instrument 100 in which an overpressure expands the balloon 104, which lets the wires 105 diverge and leads to an opening of the grab.

In contrast to this, FIGS. 4A, 4B, 4C show the situation when the balloon 104 is deflated by an underpressure, which leads to a convergent configuration of the wires 105 that closes the grab. Additionally or alternatively, the closed configuration of the grab can also be achieved by pulling the cord 101 which leads to an indentation in the tip of the balloon 104. In this case a cavity in which the instrument is located can be kept open by the inflated balloon 104 during a grabbing action.

With the described movement of the wires 105, loose cut tissue and other loose objects can be grabbed by changing the pressure inside the balloon. During the grabbing action, the overall position of the instrument will not change. Only the grabbing wires 105 will move inwards to enclose the object.

FIGS. 5 to 8 show a second embodiment of an instrument 200 that comprises an inflatable balloon 204 with filamentary, flexible tool elements 205 being partially fixed to its outside. In general, the inflatable balloon 204, its inlet 202, and a pulling cord 201 are analogous to the corresponding elements in the first embodiment and need therefore not be described again. The filamentary, flexible tool elements are now however not constituted by wires but by optical fibers 205 through which laser light can be conducted from a proximally located light source (not shown) to the outlets 206 at the distal ends of the fibers 205. Moreover, the balloon with the attached optical fibers is located in this embodiment within a catheter 210, which provides a hollow flexible tube in which the balloon 204 is free to move axially.

Figure 5:
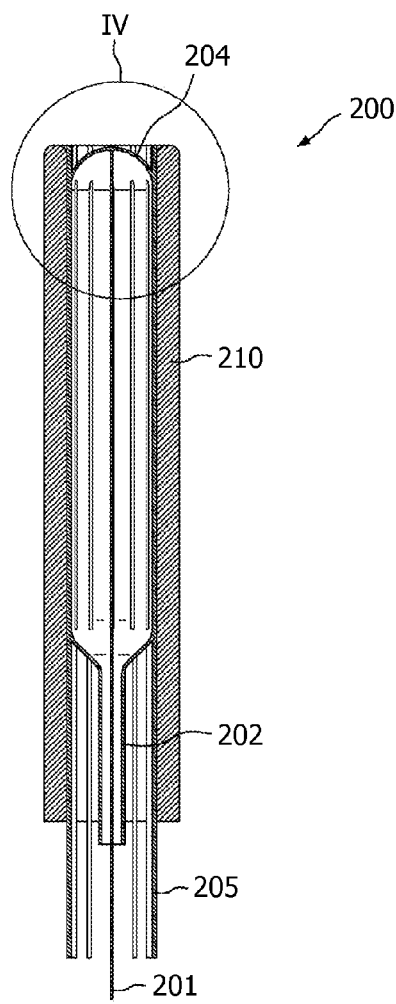
FIG. 5 shows schematically an axial section through an instrument with a plurality of optical fibers arranged circumferentially around a balloon.
Figure 6:
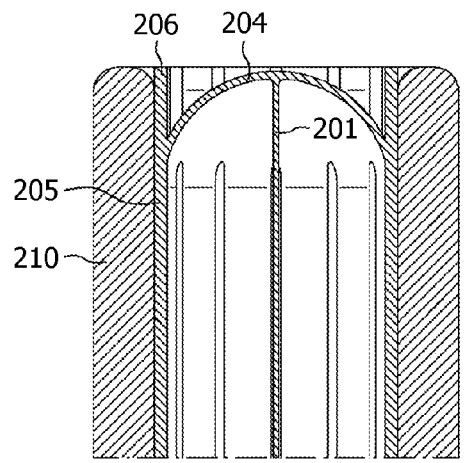
FIG. 6 shows an enlarged view of the tip area of the instrument that is encircled in FIG. 5, wherein the balloon is in its neutral configuration with the optical fibers extending axially.

Again, the inflation or deflation of the balloon 204 and/or a pulling at the cord 201 can be used to alter the shape of the balloon and thus also the direction of the optical fibers 205 and their outlets 206. FIGS. 5 and 6 show in this respect the neutral configuration in which the optical fibers are axially stretched and the emitted light is more or less straight forward concentrated on a spot with about the diameter of the catheter 210 (wherein the actual size of the spot depends on the distance between the end of the catheter and the illuminated area).

Figure 7:
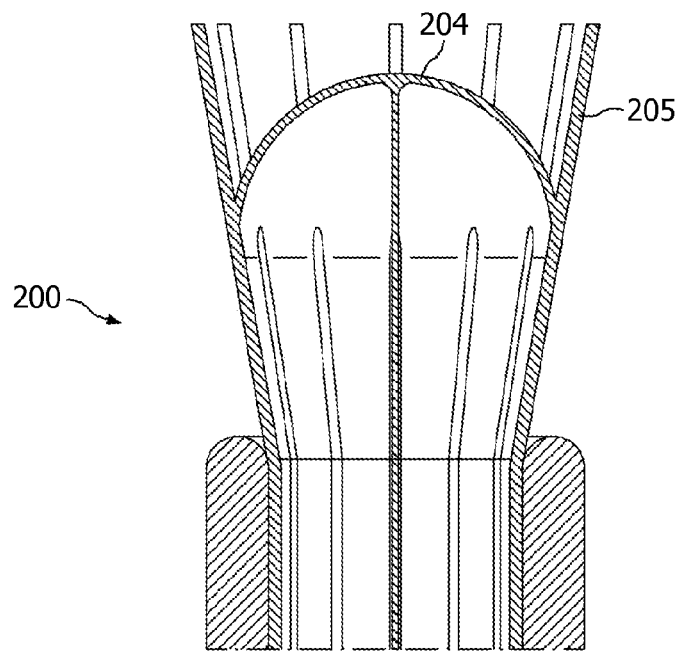
FIG. 7 shows an enlarged view of the tip of the instrument of FIG. 6 in a state in which the balloon is inflated and the optical fibers have a divergent configuration.

FIG. 7 shows a state in which the balloon 204 is pushed over a certain distance out of the catheter 210 and expanded by an overpressure, letting the optical fibers 205 diverge. In this way a larger area can be illuminated. If the expansion is larger than the area illuminated by one fiber, a circular illumination will appear with a dark spot in the middle.

Figure 8:
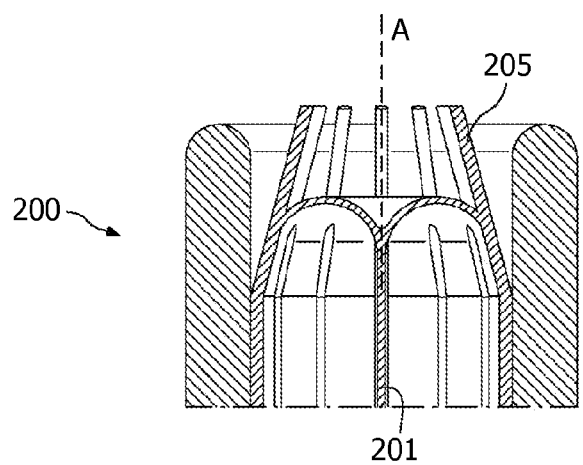
FIG. 8 shows in a similar representation as FIG. 7 the instrument when the balloon is deflated and the optical fibers converge.

FIG. 8 shows a state in which the middle of the balloon tip is pulled backwards by the cord 201 and/or in which the balloon is deflated. The fibers 205 will then bend inwards to the centre of the catheter. In this way all fibers can be aimed at the same focus point on the axis A of the instrument.

Aiming the fibers 205 towards a predetermined point can be done by directing the catheter 210 appropriately with existing catheter aiming solutions. The described variable convergence or divergence of the fibers 205 can then particularly be used to adjust the illumination area. Thus spreading the fibers will illuminate a larger area, while aiming them to one point creates a large concentration of light at said point.

The described instrument 200 can be used in medical catheter applications for illuminating tissue for several medical reasons, e.g. for coagulating or burning tissue.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. An instrument for medical procedures, comprising:
    an inflatable balloon; and
    a plurality of filamentary tool elements with at least two of the plurality of filamentary tool elements configured with a proximal movable section solely attached to a wall of the balloon, and with a distal end projecting freely from the balloon, wherein the plurality of filamentary tool elements are formed around a substantially cylindrical shape when the inflatable balloon is inflated and deflated and the distal ends bend from the substantially cylindrical shape when the balloon is inflated.

2. The instrument according to claim 1, wherein the distal end of at least one of the plurality of filamentary tool elements are radially bent inwards to a longitudinal axis of the inflatable balloon.

3. The instrument according to claim 1, wherein the plurality of filamentary tool elements comprise wire elements.

4. The instrument according to claim 3, wherein the wire elements have end portions with a barb or a bending.

5. The instrument according to claim 1, wherein at least one of the plurality of filamentary tool elements comprises an optical fiber.

6. The instrument according to claim 1, wherein the plurality of tool elements are arranged circumferentially around the balloon.

7. The instrument according to claim 1, comprising a rigid body, wherein a portion of the balloon a distance from the proximal end is attached to the rigid body.

8. The instrument according to claim 7, comprising a manipulating element connected to a distal tip of the balloon and configured for providing an indentation in the distal tip of the balloon when the balloon is inflated.

9. The instrument according to claim 8, wherein the manipulating element is one of a cord or a rod, that is fixed with one end to the distal tip of the balloon.

10. The instrument according to claim 1, comprising a tubular element in which the balloon is disposed.

11. The instrument according to claim 1, comprising an endoscope or a catheter.

12. A method of manufacturing an instrument for minimal invasive surgery, the method comprising acts of:
- providing an inflatable balloon;
- providing a plurality of filamentary tool elements; and
- attaching a proximal movable section of at least two of the plurality of filamentary tool elements solely to a wall of the balloon such that a distal end of the at least two of the plurality of filamentary tool elements project freely from the balloon, wherein the plurality of filamentary tool elements are formed around a substantially cylindrical shape when the inflatable balloon is inflated and deflated and the distal ends bend from the substantially cylindrical shape when the balloon is inflated.

* * * * *